United States Patent

Gätzi et al.

[11] 4,029,785
[45] June 14, 1977

[54] AMINO CONTAINING ISONICOTINIC ACID DERIVATIVES

[75] Inventors: Karl Gätzi; Karl Hoegerle, both of Basel, Switzerland

[73] Assignee: Ciba-Geigy Corporation, Ardsley, N.Y.

[22] Filed: Dec. 12, 1974

[21] Appl. No.: 532,145

[30] Foreign Application Priority Data

Dec. 17, 1973 Switzerland .................. 17663/73

[52] U.S. Cl. .................... 424/248.53; 424/258; 424/266; 260/247.2 R; 260/286 R; 260/293.69; 260/295 R

[51] Int. Cl.² ............... C07D 213/79; A01N 9/22

[58] Field of Search .......... 260/247.2, 295, 293.69, 260/286, 247.2, 295 R, 296 R; 424/248, 263, 258, 267, 266

[56] References Cited

UNITED STATES PATENTS 3,637,716  1/1972  Bimber et al. ............... 260/295 R

OTHER PUBLICATIONS

Temple et al., J. Heterocyclic Chemistry, vol. 7, pp. 451–452 (1970).
Sell et al., "J. Chem. Soc." vol. 71 (1897) pp. 1068–1084.

*Primary Examiner*—Henry R. Jiles
*Assistant Examiner*—R. W. Ramsuer
*Attorney, Agent, or Firm*—Frederick H. Rabin

[57] ABSTRACT

Compounds of formula

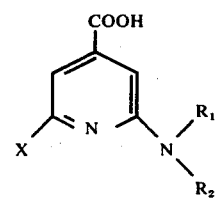

wherein
  X represents chlorine, bromine or iodine,
  $R_1$ represents a $C_1$–$C_{12}$-alkyl group optionally substituted by hydroxy, $C_1$–$C_4$-alkoxy, amino or mono- or di-$C_1$–$C_2$-alkylamino; or a $C_3$–$C_4$-alkenyl group, $C_3$–$C_8$-cycloalkyl group, benzyl group, p-acetylbenzyl group or phenethyl group, and
  $R_2$ represents hydrogen or a $C_1$–$C_4$-alkyl group or a $C_3$–$C_4$-alkenyl group, or
  $R_1$ and $R_2$ together represent a 5- to 7-membered heterocyclic group, which optionally can additionally contain an oxygen atom, as well as their salts with organic and inorganic bases which are useful as bactericides and fungicides.

32 Claims, No Drawings

AMINO CONTAINING ISONICOTINIC ACID DERIVATIVES

The present invention relates to isonicotinic acid derivatives, to processes for their production, and also to compositions and processes for the control of phytopathogenic bacteria and fungi.

The compounds of the invention correspond to formula I

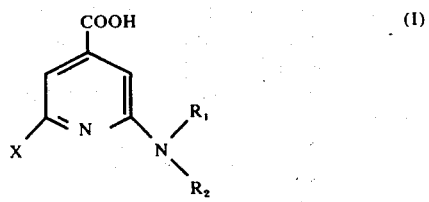

wherein
X represents chlorine, bromine or iodine,
$R_1$ represents a $C_1$–$C_{12}$-alkyl group optionally substituted by hydroxy, $C_1$–$C_4$-alkoxy, amino or mono- or di-$C_1$-$C_2$-alkylamino; or a $C_3$–$C_4$-alkenyl group, $C_3$–$C_8$-cycloalkyl group, benzyl group, p-acetylbenzyl group or phenethyl group, and
$R_2$ represents hydrogen or a $C_1$–$C_4$-alkyl group or a $C_3$–$C_4$-alkenyl group, or
$R_1$ and $R_2$ together represent a 5- to 7-membered heterocyclic group, which optionally can additionally contain an oxygen atom,
as well as their salts with organic and inorganic bases. Included with the scope of formula I are compounds in which $R_1$ represents a $C_1$–$C_{12}$ alkyl group optionally substituted by hydroxy or $C_1$–$C_4$ alkoxy, a $C_3$ or $C_4$ alkenyl group, a $C_3$–$C_6$ cycloalkyl group, benzyl group or phenethyl group.

Isonicotinic acid can also be designated as pyridine-4-carboxylic acid.

The compounds of formula I can be produced by a process in which a compound of formula II

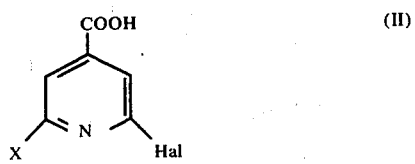

is reacted with an amine of formula III

Hal in formula II represents a halogen atom, preferably a chlorine or bromine atom, and $R_1$, $R_2$ and X have the meanings given under formula I. X and Hal preferably have the same meaning.

The process is advantageously performed in the presence of an acid-binding agent, and in the presence of a solvent which is inert to the reactants; and it is carried out at normal pressure, or at elevated pressure in a closed vessel, and at a temperature of between 20° and 170° C.

Salts are produced by known methods.

Suitable salt-forming bases are, for example, alkali metal hydroxides and alkaline-earth metal hydroxides, and nitrogen-containing bases such as ammonium bases, primary, secondary and tertiary alkylamines, guanidines, phenylethylamine, pyridine, piperidine or quinoline.

A special group of compounds by virtue of their action are those of formula I wherein $R_1$ represents a $C_1$–$C_4$-alkyl group.

Valuable compounds are also those of formula I wherein $R_1$ represents a benzyl or cyclohexyl.

The compounds of formula I wherein $R_1$ and $R_2$ together represent a piperidino or morpholino group are likewise of interest.

Other compounds of formula I having an important action are those wherein $R_2$ represents hydrogen or $C_1$–$C_4$-alkyl.

Compounds of special interest within the aforementioned groups are those wherein X represents chlorine, and also those wherein $R_2$ represents hydrogen.

A number of compounds of formula I can be used against phytopathogenic fungi. Above all, however, the compounds of formula I are suitable for the control of phytopathogenic bacteria.

Phytopathogenic bacteria that can be mentioned are, inter alia, members of the genera Pseudomonas, e.g., Pseudomonas tomato, Pseudomonas lachrymans, Pseudomonas phaseolicola, Pseudomonas tabaci and Pseudomonas syringae; Xanthomonas, e.g., Xanthomonas oryzae, Xanthomonas vesicatoria, Xanthomonas phaseoli, Xanthomonas campestri and Xanthomonas citri; and also Erwinia and Corynebacterium.

A special property of the compounds of formula I is their systemic action against phytopathogenic bacteria, i.e. their ability to be carried in a plant to a site of infection which is remote from the point of application. Thus, such a compound is able, after treatment of the soil therewith, to be absorbed by the roots of a plant and to be transported to the site of infection.

The compounds can be used on crops of useful plants, such as corn, maize, potatoes, rice, vegetables, grape vines, ornamental plants, fruit and other such crops.

In order to adapt them to suit the given circumstances, and also to broaden their range of action, the compounds of formula I can of course be used in combination with other suitable pesticides, such as fungicides, insecticides or acaricides, or with active substances that regulate plant growth.

The compounds of formula I can be used on their own or together with suitable carriers and/or other additives. Suitable carriers and additives may be solid or liquid, and they correspond to the substances common in formulation practice, such as natural or regenerated mineral substances, solvents, dispersing agents, wetting agents, adhesives, thickeners, binders or fertilisers. Such compositions are produced, in a manner known per se, by the intimate mixing and grinding of the constituents.

For application, the compounds of formula I can be formulated into the following preparations:

solid preparations: dusts, scattering agents, granulates, coated granulates, impregnated granulates and homogeneous granulates;
liquid preparations:
  a. water-dispersible active-substance concentrates: wettable powders, pastes or emulsions;

b. solutions.

The above described preparations contain between 0, 1 and 95 percent by weight of active substance.

The active substances of the formula I can be formulated for example as follows:

Wettable powders

The following constituents are used for the preparation of (a) a 40%; (b) and (c) a 25%; and (d) a 10% wettable powder:

(a)

40 parts of active substance,
5 parts of sodium lignin sulphonate,
1 part of sodium dibutyl-naphthalene sulphonate,
54 parts of silicic acid;

(b)

25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, and the mixture is then ground in the appropriate mills and rollers. There are obtained wettable powders which can be diluted with water to produce suspensions of any desired concentration.

Dusts

The following substances are used to prepare (a) a 5% dust and (b) a 2% dust:

(a)

5 parts of active substance,
95 parts of talcum;

(b)

2 parts of active substance
1 part of highly dispersed silicic acid,
97 parts of talcum.

The active substances are mixed and ground with the carriers.

Granulate

The following substances are used to produce a 5% granulate:

5 parts of active substance,
0.25 part of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The solution thus obtained is sprayed onto kaolin, and the acetone is subsequently evaporated off in vacuo.

Emulsifiable concentrates

The following substances are used to produce a 25% emulsifiable concentrate:

25 parts of active substance,
2.5 parts of epoxidised vegetable oil,
10 parts of alkylarylsulphonate/fatty alcohol polyglycol ether mixture,
5 parts of dimethylformamide,
57.5 parts of xylene.

It is possible to obtain from such concentrates, by dilution with water, emulsions of any desired concentration.

The following examples serve to further illustrate the invention, without limiting the scope thereof. Temperature values are given in degrees Centigrade.

EXAMPLE 1

Production of 2-chloro-6-methylamino-isonicotinic acid of the formula

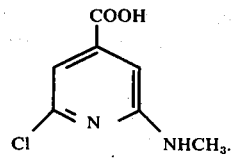

19.2 g of 2,6-dichloroisonicotinic acid (0.1 mole) is heated with 45 ml of approx. 40% aqueous monomethylamine solution and 40 ml of water in a closed tube for 10 hours at 90°–100°.

The light-yellow reaction solution is acidified with 2N hydrochloric acid to pH 4, and the precipitated product is filtered off with suction. After recrystallisation from n-propanol, the resulting 2-chloro-6-methylamino-isonicotinic acid melts at 264°–267°.

EXAMPLE 2

Production of dodecylguanidinium-2-chloro-6-methylaminoisonicotinate of the formula

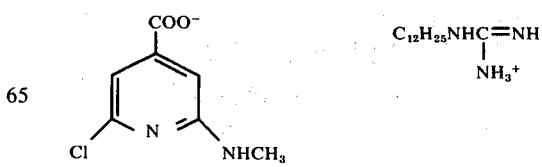

9.3 g of 2-chloro-6-methylamino-isonicotinic acid (0.05 mole) is heated with 11.3 g of dodecylguanidine (0.05 mole) in 50 ml of methanol at 60°. The solution is concentrated in vacuo to dryness, and the residue is recrystallised from acetonitrile to obtain dodecylguanidinium-2-chloro-6-methylaminoisonicotinate in the form of colourless crystals, M.P. 145°.

The following compounds are obtained in an analogous manner:

| Compound | Physical data |
| --- | --- |
| 2-chloro-6-ethylamino-isonicotinic acid | M.P. 252–4° |
| 2-chloro-6-isopropylamino-isonicotinic acid | M.P. 252–4° |
| 2-chloro-6-n-butylamino-isonicotinic acid | M.P. 231–3° |
| 2-chloro-6-pyrrolidino-isonicotinic acid | M.P. 197–200° |
| 2-chloro-6-piperidino-isonicotinic acid | M.P. 170–2° |
| 2-chloro-6-morpholino-isonicotinic acid | M.P. 225–7° |
| 2-chloro-6-benzylamino-isonicotinic acid | M.P. 242–5° |
| 2-chloro-6-cyclohexylamino-isonicotinic acid | M.P. 160–4° |
| 2-bromo-6-methylamino-isonicotinic acid | M.P. >300° |
| 2-chloro-6-$\beta$-hydroxyethylamino-isonicotinic acid | M.P. 202–5° |
| 2-chloro-6-n-propylamino-isonicotinic acid | M.P. 240–3° |
| 2-chloro-6-isobutylamino-isonicotinic acid | M.P. 253–5° |
| 2-chloro-6-sec-butylamino-isonicotinic acid | M.P. 233–5° |
| 2-chloro-6-n-pentylamino-isonicotinic acid | M.P. 227–31° |
| 2-chloro-6-(3-methyl-pent-2-yl-amino)-isonicotinic acid | M.P. 226–31° |
| 2-chloro-6-n-hexylamino-isonicotinic acid | M.P. 207–10° |
| 2-chloro-6-(hept-2-yl-amino)-iso nicotinic acid | M.P. 186–8° |
| 2-chloro-6-(2,4-dimethylpent-3-yl-amino)-isonicotinic acid | M.P. 188–91° |
| 2-chloro-6-n-octylamino-isonicotinic acid | M.P. 203–6° |
| 2-chloro-6-n-decylamino-isonicotinic acid | M.P. 207–10° |
| 2-chloro-6-n-dodecylamino-isonicotinic acid | M.P. 207–10° |
| 2-chloro-6-allylamino-isonicotinic acid | M.P. 220–2° |
| 2-chloro-6-cycloheptylamino-isonicotinic acid | M.P. 252–5° |
| 2-chloro-6-($\gamma$-hydroxy-propylamino)-isonicotinic acid | M.P. 187–91° |
| 2-chloro-6-($\beta$-aminoethylamino)-isonicotinic acid-chlorohydrate | M.P. 265–8° |
| 2-chloro-6-($\beta$-ethoxyethylamino)-isonicotinic acid | M.P. 175–9° |
| 2-chloro-6-($\gamma$-butoxypropylamino)-isonicotinic acid | M.P. 172–4° |
| 2-chloro-6-($\gamma$-dimethylamino-propylamino)-isonicotinic acid | M.P. 207–10° |
| 2-chloro-6-dimethylamino-isonicotinic acid | M.P. 164–7° |
| 2-chloro-6-diethylamino-isonicotinic acid | M.P. 154–8° |
| 2-chloro-6-di-n-butylamino-isonicotinic acid | M.P. 116–19° |
| 2-chloro-6-(benzyl-n-propylamino)-isonicotinic acid | M.P. 127–31° |
| 2-chloro-6-(p-acetylbenzyl-n-propylamino)-isonicotinic acid | M.P. 122–5° |
| 2-chloro-6-(benzyl-n-butylamino)-isonicotinic acid | M.P. 115–9° |
| 2-bromo-6-n-butylamino-isonicotinic acid | M.P. 232–5° |
| 2-bromo-6-($\beta$-hydroxyethylamino)-isonicotinic acid | M.P. 208–10° |
| 2-chloro-6-cyclopropylamino-isonicotinic acid | M.P. 236–8° |
| 2-chloro-6-phenylamino-isonicotinic acid | M.P. 238–40° |
| 2-chloro-6-diallylamino-isonicotinic acid | M.P. 107–109° |
| 2-chloro-6-($\gamma$-methylamino-propylamino)-isonicotinic acid | M.P. |
| 2-chloro-6-($\beta$-methylamino-ethylamino)-isonicotinic acid | M.P. 260–2° |

EXAMPLE 3

Action against Pseudomonas lachrymans on cucumbers and Xanthomonas vesicatoria on paprika a. Residual action (R)

Young cucumber and paprika plants are sprayed, until dripping wet, with the active substance in the form of a spray emulsion containing 1000 ppm of active substance.

One day after application of the spray emulsion, the plants are infested, by spraying of the underside of the primary leaves, with suspensions of the respective bacteria, and subsequently incubated for 8 days at 22° C and 95% relative humidity. After this period of time, an evaluation is made on the basis of the number of typical disease spots.

b. Systemic action (S)

Young cucumber and paprika plants are watered with the active substance in the form of a suspension of the active substance (concentration 100 ppm relative to the pot soil).

One day after application of the suspension, the plants are infested, by spraying of the underside of the primary leaves, with suspensions of the respective bacteria, and then incubated for 8 days at 22° C and 95% relative humidity. After this period of time, an evaluation is made on the basis of the number of typical disease spots.

The following isonicotinic acid derivatives exhibited in the case of the given bacteria a good action (i.e.

plants less than 20% infested, compared with untreated but infested control plants).

| Compound | Pseudomonas lachrymans | | Xanthomonas vesicatoria | |
|---|---|---|---|---|
| | R | S | R | S |
| 2-chloro-6-methylamino-isonicotinic acid | + | | + | |
| 2-chloro-6-n-butylamino-isonicotinic acid | + | + | + | + |
| 2-chloro-6-isopropylamino-isonicotinic acid | + | + | + | + |
| 2-chloro-6-piperidino-isonicotinic acid | + | + | + | |
| 2-chloro-6-morpholino-isonicotinic acid | + | + | + | + |
| 2-bromo-6-methylamino-isonicotinic acid | + | + | | |
| 2-chloro-6-n-hexylamino-isonicotinic acid | + | + | + | + |
| 2-chloro-6-cyclohexylamino-isonicotinic acid | + | | | |
| 2-chloro-6-benzylamino-isonicotinic acid | + | + | + | + |
| 2-chloro-6-($\beta$-hydroxyethylamino)-isonicotinic acid | + | + | + | + |
| 2-chloro-6-diethylamino-isonicotinic acid | + | + | + | + |
| 2-chloro-6-isobutylamino-isonicotinic acid | | + | | |
| 2-chloro-6-n-pentylamino-isonicotinic acid | + | + | | + |

What we claim is:
1. A compound of the formula

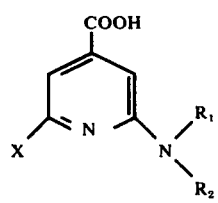

wherein
X represents chlorine, bromine or iodine,
$R_1$ represents $C_1$–$C_{12}$ alkyl, $C_1$–$C_{12}$ hydroxyalkyl, $C_1$–$C_{12}$ alkyl substituted by $C_1$–$C_4$ alkoxy, $C_1$–$C_{12}$ aminoalkyl, $C_1$–$C_{12}$ alkyl substituted by mono- or di-($C_1$ or $C_2$ alkyl)amino, $C_3$ or $C_4$ alkenyl, $C_3$–$C_8$ cycloalkyl, benzyl, p-acetylbenzyl or phenethyl, and
$R_2$ represents hydrogen, $C_1$–$C_4$ alkyl, or $C_3$ or $C_4$ alkenyl, or
$R_1$ and $R_2$ taken together with the nitrogen atom to which they are attached represent morpholino, piperidino or pyrrolidino, or a salt thereof with a suitable organic or inorganic base.
2. A compound according to claim 1 in which
$R_1$ represents $C_1$–$C_{12}$ alkyl, $C_1$–$C_{12}$ hydroxyalkyl, $C_1$–$C_{12}$ alkyl substituted by $C_1$–$C_4$ alkoxy, $C_3$ or $C_4$ alkenyl, $C_3$–$C_6$ cycloalkyl, benzyl, or phenethyl, and
$R_2$ represents hydrogen, $C_1$–$C_4$ alkyl or $C_3$ or $C_4$ alkenyl, or
$R_1$ and $R_2$ taken together with the nitrogen atom to which they are attached represent morpholino, piperidino or pyrrolidino.
3. A compound according to claim 2 in which $R_1$ represents $C_1$–$C_4$ alkyl.
4. A compound according to claim 2 in which $R_1$ represents benzyl or cyclohexyl.
5. A compound according to claim 1 in which $R_1$ and $R_2$ taken together with the nitrogen atom to which they are attached represent piperidino or morpholino.
6. A compound according to claim 1 in which $R_2$ represents hydrogen.
7. A compound according to claim 2 in which $R_2$ represents hydrogen.
8. A compound according to claim 2 in which $R_2$ represents $C_1$–$C_4$ alkyl.
9. A compound according to claim 1 in which X represents chlorine.
10. 2-Chloro-6-methylamino-isonicotinic acid.
11. 2-Chloro-6-n-butylamino-isonicotinic acid.
12. 2-Chloro-6-n-hexylamino-isonicotinic acid.
13. 2-Chloro-6-cyclohexylamino-isonicotinic acid.
14. 2-Chloro-6-benzylamino-isonicotinic acid.
15. 2-Chloro-6-diethylamino-isonicotinic acid.
16. 2-Chloro-6-morpholino-isonicotinic acid.
17. A composition for inhibiting the growth of phytopathogenic bacteria and fungi comprising a bactericidally or fungicidally effective amount of (1) a compound according to claim 1 and (2) a carrier.
18. A method for inhibiting the growth of phytopathogenic fungi and bacteria which comprises applying thereto an effective amount of a compound according to claim 1.
19. A method for inhibiting the growth of phytopathogenic bacteria which comprises applying thereto an effective amount of a compound according to claim 1.
20. A method according to claim 19 in which, in the compound, $R_1$ represents $C_1$–$C_4$ alkyl.
21. A method according to claim 19 in which, in the compound, $R_1$ represents benzyl or cyclohexyl.
22. A method according to claim 19 in which, in the compound, $R_1$ and $R_2$ taken together with the nitrogen atom to which they are attached, represent piperidino or morpholino.
23. A method according to claim 19 in which, in the compound, $R_2$ represents hydrogen.
24. A method according to claim 19 in which, in the compound, $R_2$ represents $C_1$–$C_4$ alkyl.
25. A method according to claim 20 in which the compound is 2-chloro-6-methylamino-isonicotinic acid.
26. A method according to claim 20 in which the compound is 2-chloro-6-n-butylamino-isonicotinic acid.
27. A method according to claim 19 in which the compound is 2-chloro-6-n-hexylamino-isonicotinic acid.
28. A method according to claim 21 in which the compound is 2-chloro-6-cyclohexylamino-isonicotinic acid.
29. A method according to claim 21 in which the compound is 2-chloro-6-benzylamino-isonicotinic acid.
30. A compound according to claim 19 in which the compound is 2-chloro-6-diethylamino-isonicotinic acid.
31. A method according to claim 22 in which the compound is 2-chloro-6-morpholino-isonicotinic acid.
32. A method according to claim 19 in which, in the compound, X represents chlorine.

* * * * *